(12) United States Patent
Valderrabano et al.

(10) Patent No.: US 10,398,562 B2
(45) Date of Patent: Sep. 3, 2019

(54) TALAR IMPLANT FOR MODIFYING JOINT KINEMATICS

(71) Applicant: EXACTECH, INC., Gainesville, FL (US)

(72) Inventors: Victor Valderrabano, Hofstetten (CH); James Nunley, Durham, NC (US); James DeOrio, Durham, NC (US); Mark Easley, Durham, NC (US); Matthew Hamilton, Gainesville, FL (US); Phong Diep, Gainesville, FL (US)

(73) Assignee: Exactech, Inc., Gainesville, FL (US)

( * ) Notice: Subject to any disclaimer, the term of this patent is extended or adjusted under 35 U.S.C. 154(b) by 21 days.

(21) Appl. No.: 15/544,774

(22) PCT Filed: Jan. 20, 2016

(86) PCT No.: PCT/US2016/014078
§ 371 (c)(1),
(2) Date: Jul. 19, 2017

(87) PCT Pub. No.: WO2017/127067
PCT Pub. Date: Jul. 27, 2017

(65) Prior Publication Data
US 2018/0098858 A1    Apr. 12, 2018

Related U.S. Application Data

(60) Provisional application No. 62/105,361, filed on Jan. 20, 2015.

(51) Int. Cl.
*A61F 2/42*    (2006.01)
*A61F 2/46*    (2006.01)
(Continued)

(52) U.S. Cl.
CPC .......... *A61F 2/4202* (2013.01); *A61F 2/4606* (2013.01); *A61B 17/7291* (2013.01);
(Continued)

(58) Field of Classification Search
CPC ...... A61F 2002/4207; A61F 2002/4205; A61F 2/4202; A61F 2002/4212; A61F 2/42;
(Continued)

(56) References Cited

U.S. PATENT DOCUMENTS 4,069,518 A * 1/1978 Groth, Jr. .............. A61F 2/4202
  623/21.18
4,470,158 A * 9/1984 Pappas .................. A61F 2/3804
  623/20.2

(Continued)

OTHER PUBLICATIONS

Hayes, et al., Ankle morphometry on 3D-CT images, University of Iowa Dept. of Orthopaedics and Rehabilitation, vol. 26, pp. 1-3, 2006.

(Continued)

*Primary Examiner* — Alvin J Stewart
(74) *Attorney, Agent, or Firm* — Greenberg Traurig, LLP (57) ABSTRACT

A talar implant, comprising: a superior surface, defined by an arc having at least one first radius; an inferior surface, defined by an arc having at least one second radius, a lateral side; a medial side; a posterior portion having a first width; and an anterior portion having a second width; wherein the implant is configured to restore a tibio-talar joint tension, wherein the superior surface is separated from the inferior surface by a thickness, wherein the at least one first radius is smaller than the at least one second radius, wherein the center of the arc having at least one first radius is offset from the center of the arc having at least one second radius in at (Continued)

least one plane of the talar implant, and wherein the anterior portion further comprises an extension configured to provide support.

17 Claims, 11 Drawing Sheets

(51) Int. Cl.
  *A61F 2/30* (2006.01)
  *A61B 17/72* (2006.01)
  *A61F 2/28* (2006.01)

(52) U.S. Cl.
  CPC .............. *A61F 2002/2871* (2013.01); *A61F 2002/30878* (2013.01); *A61F 2002/30934* (2013.01); *A61F 2002/4207* (2013.01)

(58) Field of Classification Search
  CPC ............ A61F 2/38; A61F 2/3804; A61F 2002/30123; A61F 2/4261; A61F 2/4425; A61F 2002/443
  See application file for complete search history.

(56) References Cited

U.S. PATENT DOCUMENTS

| | | | | |
|---|---|---|---|---|
| 4,755,185 | A * | 7/1988 | Tarr | A61F 2/4202 623/23.4 |
| 6,409,767 | B1 * | 6/2002 | Perice | A61F 2/4202 623/21.18 |
| 7,323,012 | B1 * | 1/2008 | Stone | A61F 2/4202 623/21.18 |
| 9,700,424 | B2 * | 7/2017 | Sanders | A61F 2/4225 |
| 2003/0181985 | A1 * | 9/2003 | Keller | A61F 2/4202 623/21.18 |
| 2006/0142870 | A1 * | 6/2006 | Robinson | A61B 17/15 623/21.18 |
| 2006/0229730 | A1 * | 10/2006 | Railey | A61B 17/15 623/21.18 |
| 2007/0027547 | A1 * | 2/2007 | Rydell | A61B 17/562 623/21.18 |
| 2007/0173944 | A1 * | 7/2007 | Keller | A61F 2/4202 623/18.11 |
| 2008/0097617 | A1 * | 4/2008 | Fellinger | A61F 2/4202 623/21.18 |
| 2008/0306604 | A1 * | 12/2008 | Parenti Castelli | A61F 2/38 623/20.21 |
| 2009/0082875 | A1 | 3/2009 | Long | |
| 2009/0088846 | A1 * | 4/2009 | Myung | A61F 2/30756 623/14.12 |
| 2010/0057216 | A1 * | 3/2010 | Gannoe | A61F 2/4202 623/21.18 |
| 2012/0109326 | A1 * | 5/2012 | Perler | A61F 2/4202 623/21.18 |
| 2012/0123553 | A1 * | 5/2012 | Sidebotham | A61F 2/30771 623/23.15 |
| 2014/0018814 | A1 * | 1/2014 | Gillard | A61F 2/4202 606/93 |
| 2014/0018931 | A1 * | 1/2014 | Gillard | A61F 2/30771 623/21.18 |
| 2014/0128985 | A1 * | 5/2014 | Sanders | A61F 2/4225 623/21.18 |
| 2014/0188230 | A1 * | 7/2014 | Rogachefsky | A61F 2/4261 623/18.12 |
| 2014/0276853 | A1 | 9/2014 | Long et al. | |
| 2014/0350688 | A1 * | 11/2014 | Michel | A61F 2/4202 623/21.18 |
| 2015/0051706 | A1 * | 2/2015 | Schon | A61F 2/4202 623/21.18 |
| 2015/0057761 | A1 * | 2/2015 | Smirthwaite | A61F 2/4202 623/21.18 |
| 2015/0320567 | A1 * | 11/2015 | Terrill | A61F 2/4202 623/21.18 |
| 2016/0128842 | A1 * | 5/2016 | Wong | A61F 2/4202 623/21.18 |
| 2016/0338841 | A1 * | 11/2016 | Sander | A61B 17/1739 |
| 2017/0056189 | A1 * | 3/2017 | Dhillon | A61F 2/30749 |
| 2017/0143500 | A1 * | 5/2017 | Impero | A61F 2/4202 |
| 2017/0304065 | A1 * | 10/2017 | Sanders | A61F 2/4225 |
| 2019/0059917 | A1 * | 2/2019 | Saltzman | A61B 17/1775 |
| 2019/0070012 | A1 * | 3/2019 | Leemrijse | A61F 2/4202 |

OTHER PUBLICATIONS

International Search Report for PCT Application No. PCT/US2016/014078, dated May 6, 2016.

\* cited by examiner

TALAR IMPLANT FOR MODIFYING JOINT KINEMATICS

CROSS REFERENCE TO RELATED APPLICATIONS

This application is a 371 National Phase Application of International Application No. PCT/US2016/014078, filed Jan. 20, 2016, which claims priority to U.S. Provisional Patent Application Ser. No. 62/105,361, filed on Jan. 20, 2015, the contents of both of which are incorporated by reference in their entireties.

FIELD

The present invention relates to talar implants configured to restore tension to the tibio-talar joint in the neutral position. In particular, the present invention provides talar implants wherein the articular surface of the talar implant is configured to reconstruct the talar dome, and wherein inferior surface of the implants are configured to preserve talar bone.

BACKGROUND

Post-traumatic osteoarthritis ("OA") in the ankle is the most common form of OA occurring in the ankle joint. Degeneration is usually caused by malalignment in the joint, resulting from bony or soft tissue injury (e.g. fracture or recurrent sprains), leading to asymmetric loading in the joint and degeneration of the cartilage. Once the cartilage is lost, the bone-on-bone articulation deforms the articular surfaces of the joint through plastic deformation and osteophyte formation and alters joint kinematics.

SUMMARY

In one embodiment, the present invention provides a talar implant, comprising:
a. a superior surface, defined by an arc having at least one first radius;
b. an inferior surface, defined by an arc having at least one second radius,
c. a lateral side;
d. a medial side;
e. a posterior portion having a first width; and
f. an anterior portion having a second width;
wherein the implant is configured to restore a joint tension between a tibio-talar joint in a neutral position,
wherein the superior surface is separated from the inferior surface by a thickness, defining a height of the medial and lateral sides,
wherein the at least one first radius is smaller than the at least one second radius,
wherein the center of the arc having at least one first radius is offset from the center of the arc having at least one second radius in at least one plane of the talar implant selected from the group consisting of: a superior/inferior plane, an anterior/posterior plane, and a medial/lateral plane,
wherein the inferior surface is configured to attach to a superior surface of the talus, and
wherein the anterior portion further comprises an extension configured to provide support.

In one embodiment, the superior surface of the implant is bicondylar. In one embodiment, the at least one first radius varies from the medial side of the implant to the lateral side of the implant.

In one embodiment, the at least one second radius varies from the medial side of the implant to the lateral side of the implant.

In one embodiment, the inferior surface further comprises at least one peg configured to anchor the talar implant to the superior surface of the talus.

In one embodiment, the center of the arc having at least one first radius is offset from the center of the arc having at least one second radius in the superior/inferior plane.

In one embodiment, the center of the arc having at least one first radius is offset from the center of the arc having at least one second radius in the anterior/posterior plane.

In one embodiment, the center of the arc having at least one first radius is offset from the center of the arc having at least one second radius in the medial/lateral plane.

In one embodiment, the offset of the center of the arc having at least one first radius from the center of the arc having at least one second radius is different on the superior surface of the implant than the offset on the inferior surface of the implant.

In one embodiment, the offset of the center of the arc having at least one first radius from the center of the arc having at least one second radius is different on the medial side of the implant than the offset on the lateral side of the implant.

In one embodiment, the offset of the center of the arc having at least one first radius from the center of the arc having at least one second radius is different on the superior portion of the implant than the offset on the anterior portion of the implant.

In one embodiment, the ratio of the at least one first radius to the at least one second radius is less than 1.

In one embodiment, the at least one first radius is from 15.0 mm to 20.0 mm.

In one embodiment, the at least one second radius is from 22.0 mm to 30.0 mm.

In one embodiment, the present invention provides a kit, comprising a plurality of talar implants,
wherein an individual talar implant of claim 1 within the plurality differs in at least one property selected from the group consisting of: the at least one first radius, the at least one second radius, the first width, the second width, the offset of the center of the arc having at least one first radius from the center of the arc having at least one second radius in the superior/inferior plane, the offset of the center of the arc having at least one first radius from the center of the arc having at least one second radius in the anterior/posterior plane, and the offset of the center of the arc having at least one first radius from the center of the arc having at least one second radius in the medial/lateral plane, from any of the other individual talar implants of claim 1 within the plurality.

In one embodiment, the kit further comprises a tibial base component.

BRIEF DESCRIPTION OF THE DRAWINGS

FIG. 2 shows a lateral view (A), and a medial view (B) of the typical arrangement of ligaments of a human tibio-talar joint.

FIG. 3 shows a lateral view (A), and a medial view (B) of the typical arrangement of the musculature of a human tibio-talar joint.

FIG. 4 shows an anterior view (A), and a lateral view (B) of the typical arrangement of the musculature of a human tibio-talar joint.

FIG. 5 shows an illustration of a colpased talar dome caused by arthritic changes (A), and restoration of the talar dome according to some embodiments of the present invention (B). $r_1$ and $r_2$ are arcs aligned along the sagittal plane, defining the articular surface ($r_1$) and inferior surface ($r_2$) of the talar implant according to some embodiments of the present invention.

FIG. 8 shows a lateral view (A) and a medial view (B) of a talar implant according to some embodiments of the present invention.

DETAILED DESCRIPTION

For clarity of disclosure, and not by way of limitation, the detailed description of the invention is divided into the following subsections that describe or illustrate certain features, embodiments or applications of the present invention.

Figure 1:
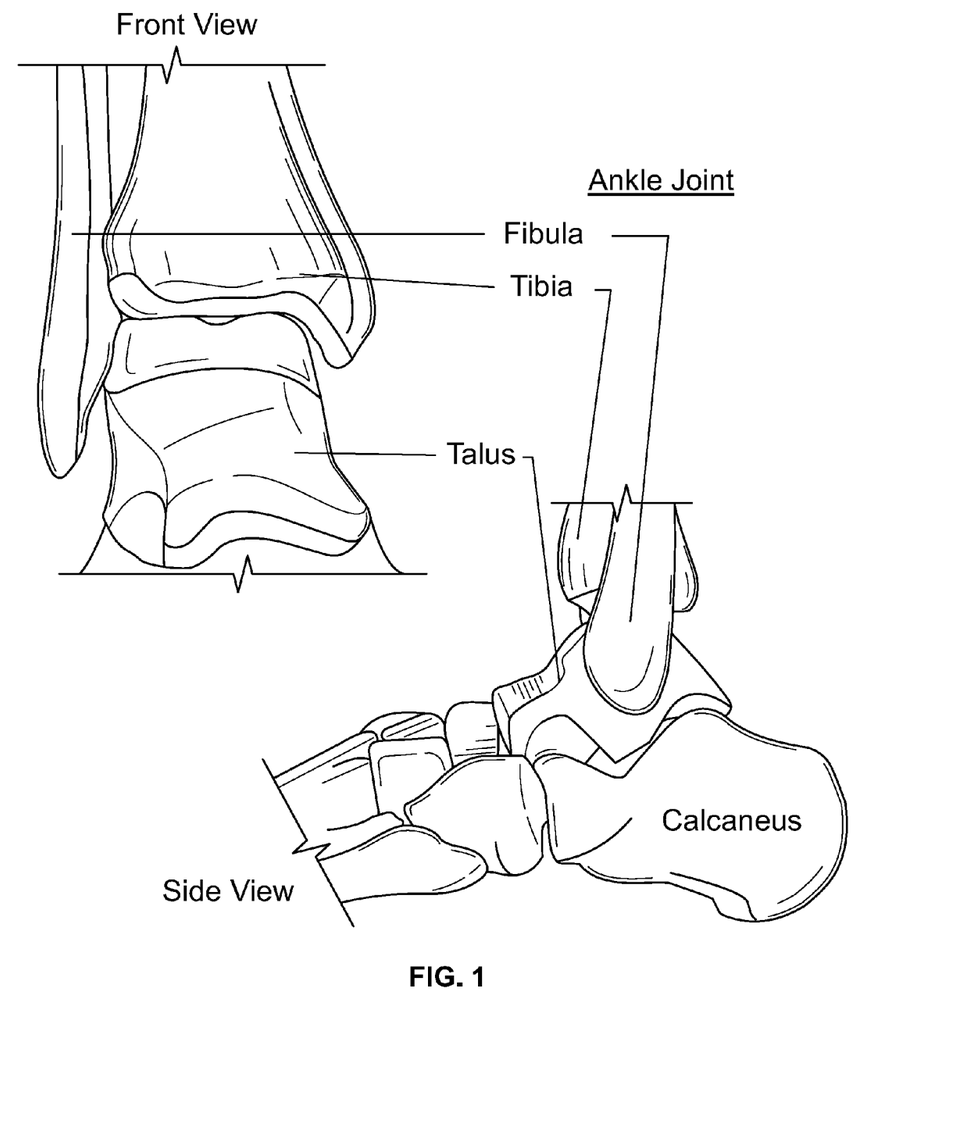
FIG. 1 shows the typical anatomy of a human ankle joint.

Referring to FIG. 1, the ankle joint is made up primarily of six bones; the talus, navicular bone, tibia, calcaneus, cuboid, and fibula. A majority of the flexion motion (approximately 75%) comes from the tibio-talar joint, the remainder (approximately 25%) is produced in the forefoot. The inversion/eversion motion comes primarily from the subtalar joint (articulation between the underside of the talus and the calcaneus).

Figure 2A:
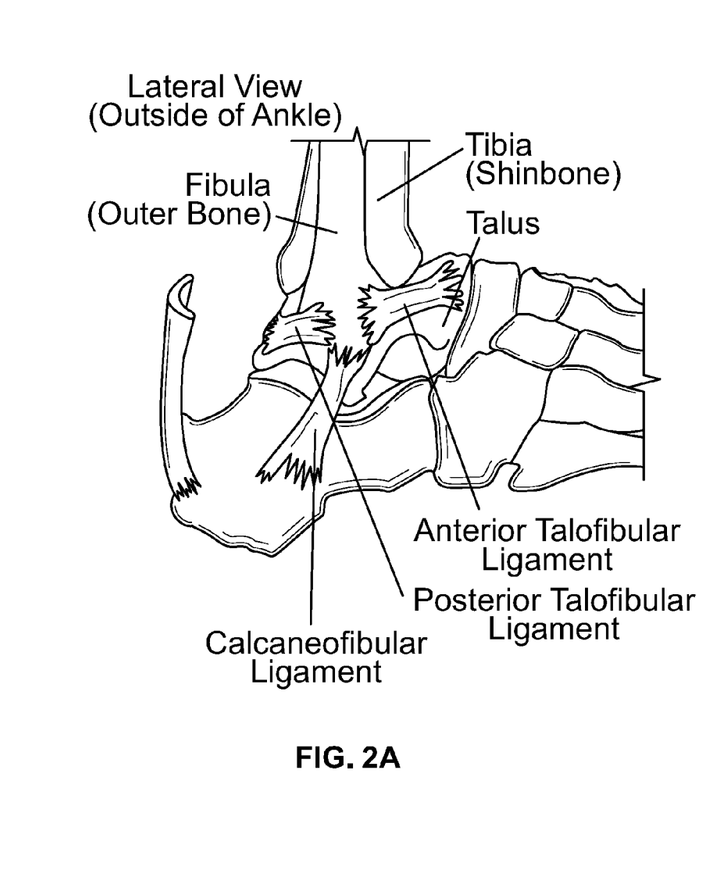
Figure 2B:
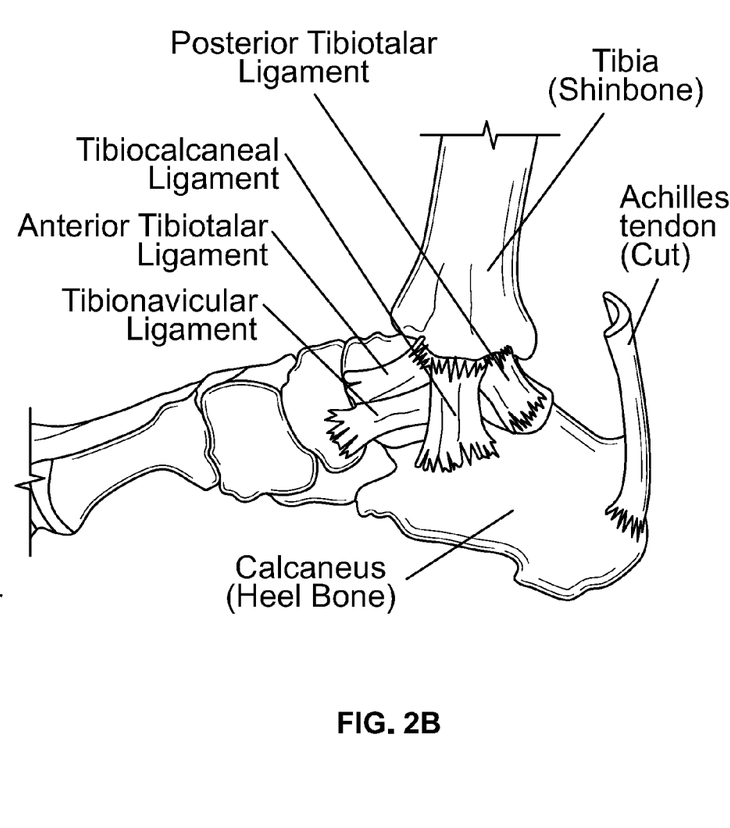

The ligamentous structures surrounding the tibio-talar joint (also referred to as the talocrural joint) act to stabilize the joint through the range of motion. The medial side of the joint is covered by a large group of ligaments referred to as the deltoid ligament. This is comprised of three different ligaments, the posterior tibiotalar (PTT) ligament, tibiocalcaneal (TC) ligament, anterior tibiotalar (ATT) ligament (see FIG. 2B). The lateral side has three primary ligaments, the anterior talofibular (ATF) ligament, calcaneofibular (CF) ligament, and posterior talofibular (PTF) ligament (see FIG. 2A). The TC ligament on the medial side and the CF ligament on the lateral side remain roughly isometric throughout the range of motion. This allows for calculating the two-dimensional instant center of the joint through the range of motion. Without being limited to any particular theory, it is believed that the tibio-talar joint moves in a combination of rolling and sliding. However, a rough approximation of the instant centers on the medial and lateral side are the middle of the TC ligament and the tip of the lateral facet (just distal to the tip of the fibula) respectively. Connecting these points forms the "axis" of the ankle joint throughout the range of motion.

Figure 3A:
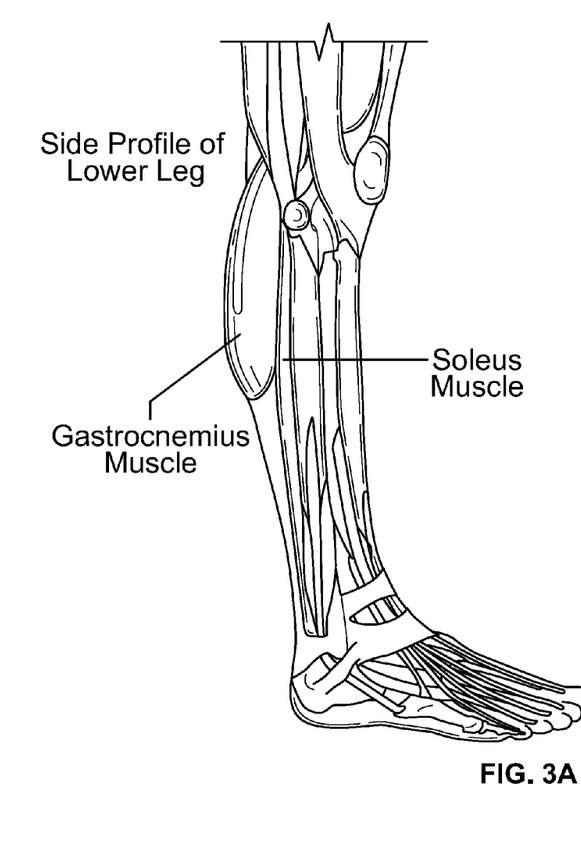
Figure 3B:
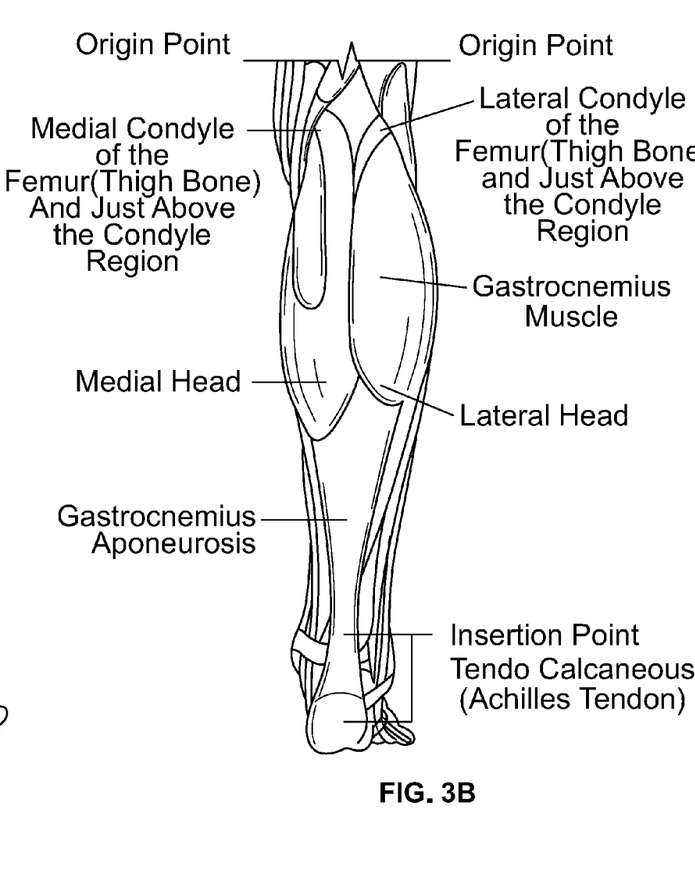
Figure 4A:
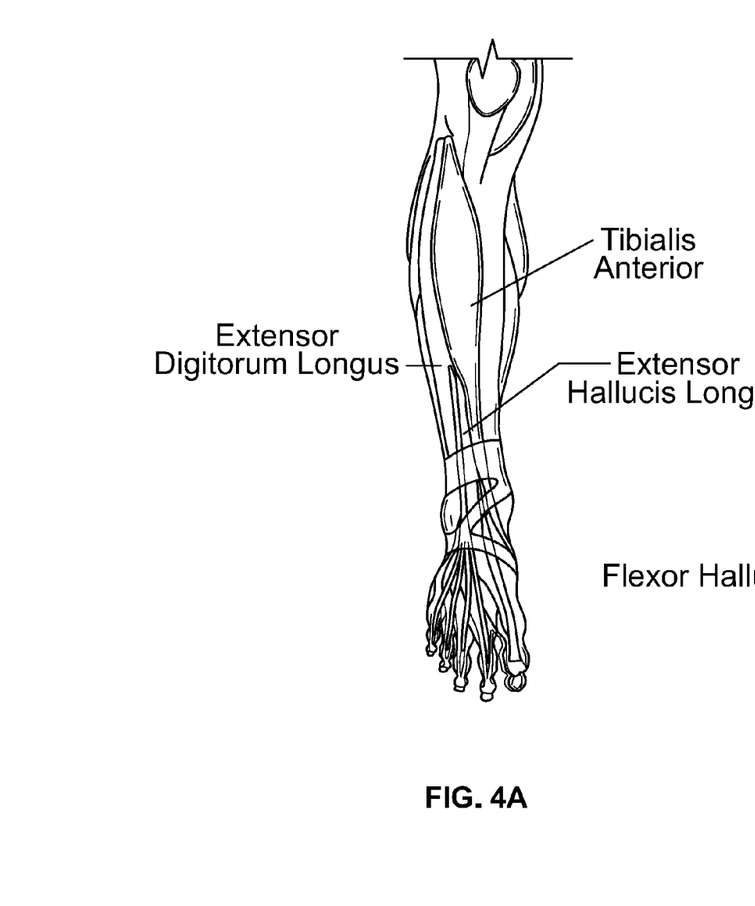
Figure 4B:
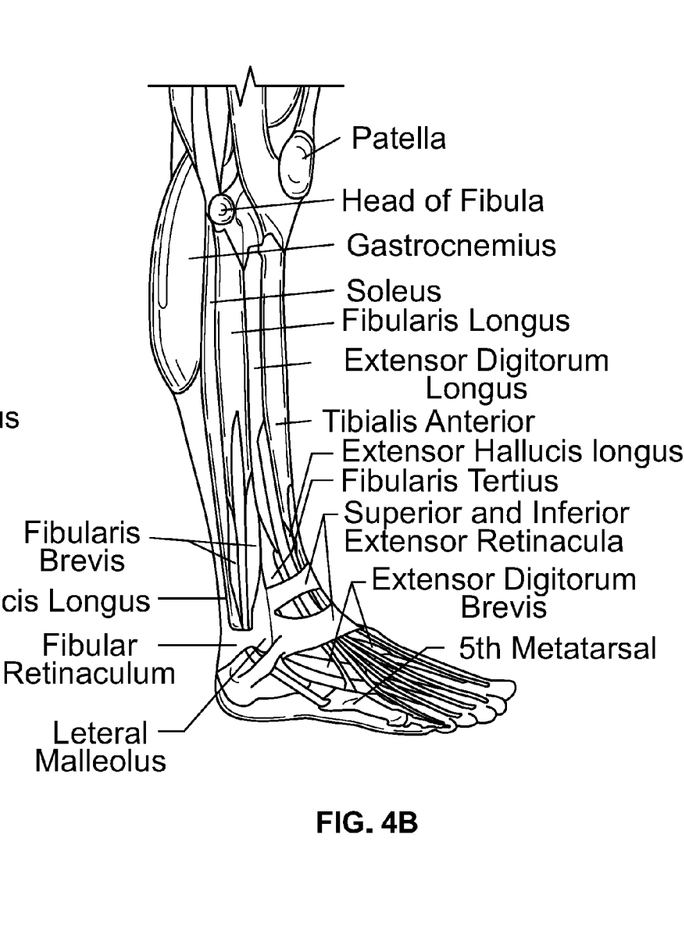

FIGS. 3A and 3B illustrate the posterior and lateral muscular structures surrounding the ankle joint. FIGS. 4A and 4B illustrate the anterior and lateral muscles surrounding the ankle joint. The primary plantarflexor of the ankle is the gastrocnemius muscle, which attaches to the posterior calcaneus through the Achilles tendon. Dorsiflexion is driven by a combination of the extensor digitorum longus and extensor hallucis longus. While these muscles insert to the anterior of the foot, the retinacula (both superior and inferior) act to contour the ligaments to the foot and limit the moment arm of the muscles relative to the talocrural joint.

Figure 5A:
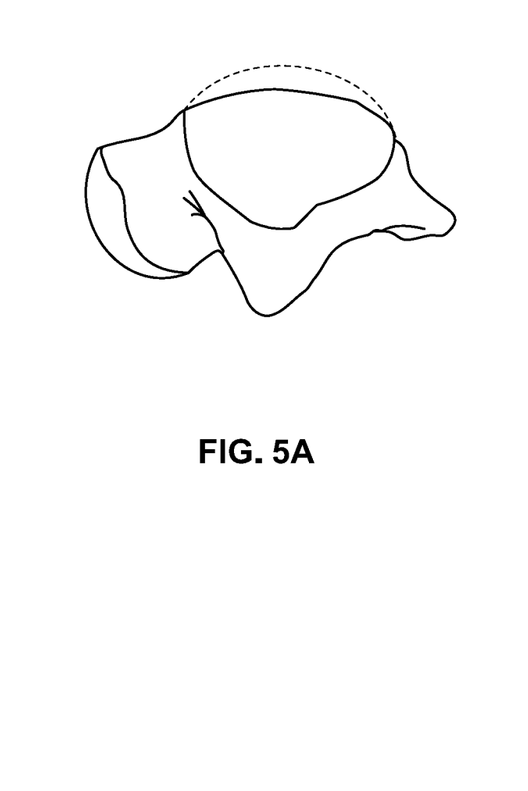
Figure 5B:
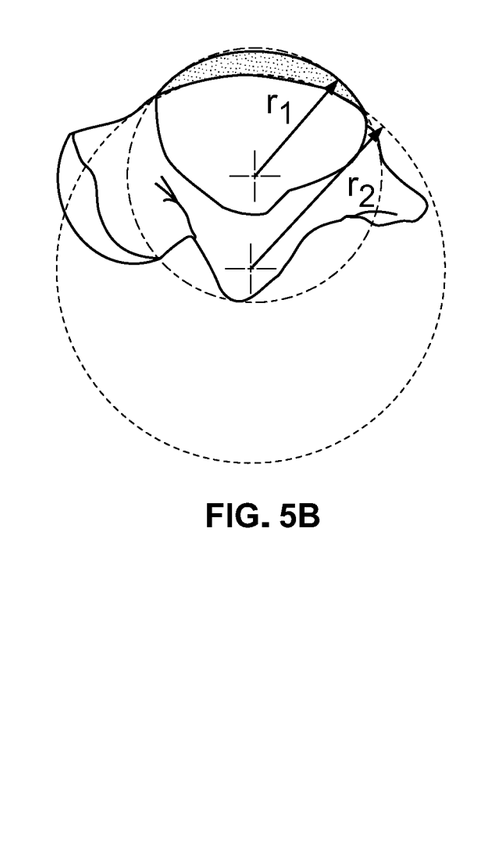

Post-traumatic osteoarthritis ("OA") in the ankle is the most common form of OA occurring in the ankle joint. Degeneration is usually caused by malalignment in the joint, resulting from bony or soft tissue injury (e.g. fracture or recurrent sprains), leading to asymmetric loading in the joint and degeneration of the cartilage. Once the cartilage is lost, the bone-on-bone articulation deforms the articular surfaces of the joint through plastic deformation and osteophyte formation and alters joint kinematics. Typically, the tibial plafond expands in the A/P dimension as it is flattened by bone-on-bone articulation. Simultaneously, the talus collapses and flattens (see FIG. 5A) to maintain congruency with the new shape of the tibial plafond.

Flattening the articular surfaces changes the position of the center of rotation through the range of motion by shifting it distal relative to its natural position. The collapse shortens the ligaments that are in line with the tibial shaft (primarily the TC ligament and the CF ligament). Reducing this distance shifts the joint line distally and creates laxity in the ligaments allowing the talus to slide in the anterior and posterior as opposed to rotating properly. When the talus is free to slide in the anterior-posterior ("A/P") direction, there is less constraint so the muscles produce less rotation of the foot during gait. The cycle of deformation of the bone driving kinematic changes which induce further deformation creates a positive feedback loop that can severely alter joint function. The shifted joint line and flattened joint motion alter the kinematics which is further compounded by the pain caused by the arthritic changes. The outcome for patients is a contracted gait cycle combined with modified movement strategies to help protect the affected joint. The typical range of motion for healthy ankle joints is greater than 30° while arthritic ankles may be closer to half of that (i.e. 18°).

Figure 6:
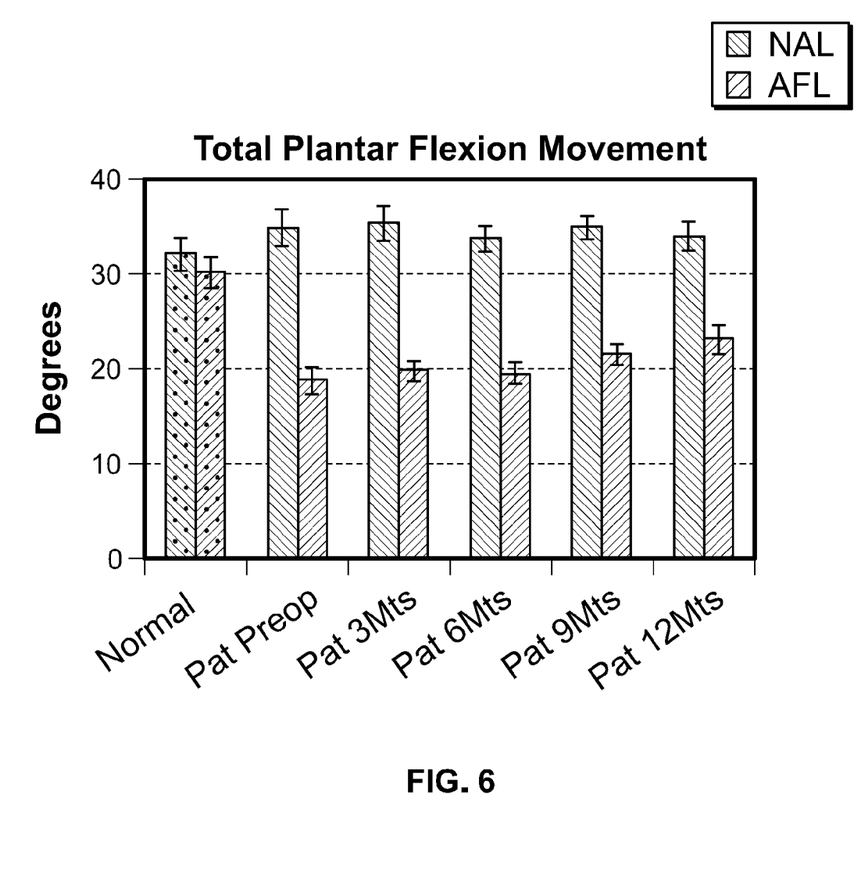
FIG. 6 shows a comparison of normal ankle plantarflexion and dorsiflexion to patients with OA pre and post total ankle replacement. NAL=Non-affected limb; AFL=Affected limb.

With other joints, removing the pain from the joint results in improved function as seen by studies in knees, hips, and shoulders. However, in many cases, the function of the ankle joint does not return to the level of the unaffected side post-operatively indicating the functional loss is not solely caused by pain in the joint (see FIG. 6). This is not limited to active range of motion, often intraoperative motion checks demonstrate a restricted motion due to ligament tension around the joint.

Without being limited to any particular theory, it is believed that the tension of the joint in plantarflexion and dorsiflexion is related to the sagittal shape of an implant body and articular geometries. Overtensioning the ligaments surrounding the ankle joint can lead to motion restriction.

Without being limited to theory, one possible explanation for the reduced restoration of function may be due to implant design. In particular, the tension of the joint in plantarflexion and dorsiflexion angle may be related to the sagittal shape of the articular geometry. Overtensioning the ligaments surrounding the ankle joint can lead to motion restriction.

For example, using an implant having a uniform thickness, or a chamfer cut inferior surface may require a volume of bone to be removed from the talus. In these instances, failure to remove bone may result in a reconstructed articular surface having an articular curvature that is greater than native anatomy.

In some embodiments, the present invention provides a talar implant, comprising:
  a. a superior surface, defined by an arc having at least one first radius;
  b. an inferior surface, defined by an arc having at least one second radius,
  c. a lateral side;
  d. a medial side;
  e. a posterior portion having a first width; and
  f. an anterior portion having a second width;
    wherein the implant is configured to restore a joint tension between a tibio-talar joint in a neutral position,
    wherein the superior surface is separated from the inferior surface by a thickness, defining a height of the medial and lateral sides,
    wherein the at least one first radius is smaller than the at least one second radius,
    wherein the center of the arc having at least one first radius is offset from the center of the arc having at least one second radius in at least one plane of the talar implant selected from the group consisting of: a superior/inferior plane, an anterior/posterior plane, and a medial/lateral plane,
    wherein the inferior surface is configured to attach to a superior surface of the talus, and
    wherein the anterior portion further comprises an extension configured to provide support.

Without intending to be limited by any particular theory, a talar implant with the superior surface and inferior surfaces being defined with arcs having different radii of curvature may preserve bone stock in the talus and restore the articular surface of the talar dome.

According to some embodiments, a talar implant of the present invention is sufficiently designed to restore the joint line and maximum tension at the center of the range of motion with the potential to reduce that tension as the joint rotates in the flexion direction. In some embodiments, a talar implant of the present invention has a thickness, that decreases in the anterior and posterior direction. In some embodiments, the decrease in thickness of the implant at the anterior and posterior portions acts to reduce joint tension at the extremes of motion and prevent the joint from being overconstrained without the need for additional ligamentous procedures.

Figure 7:
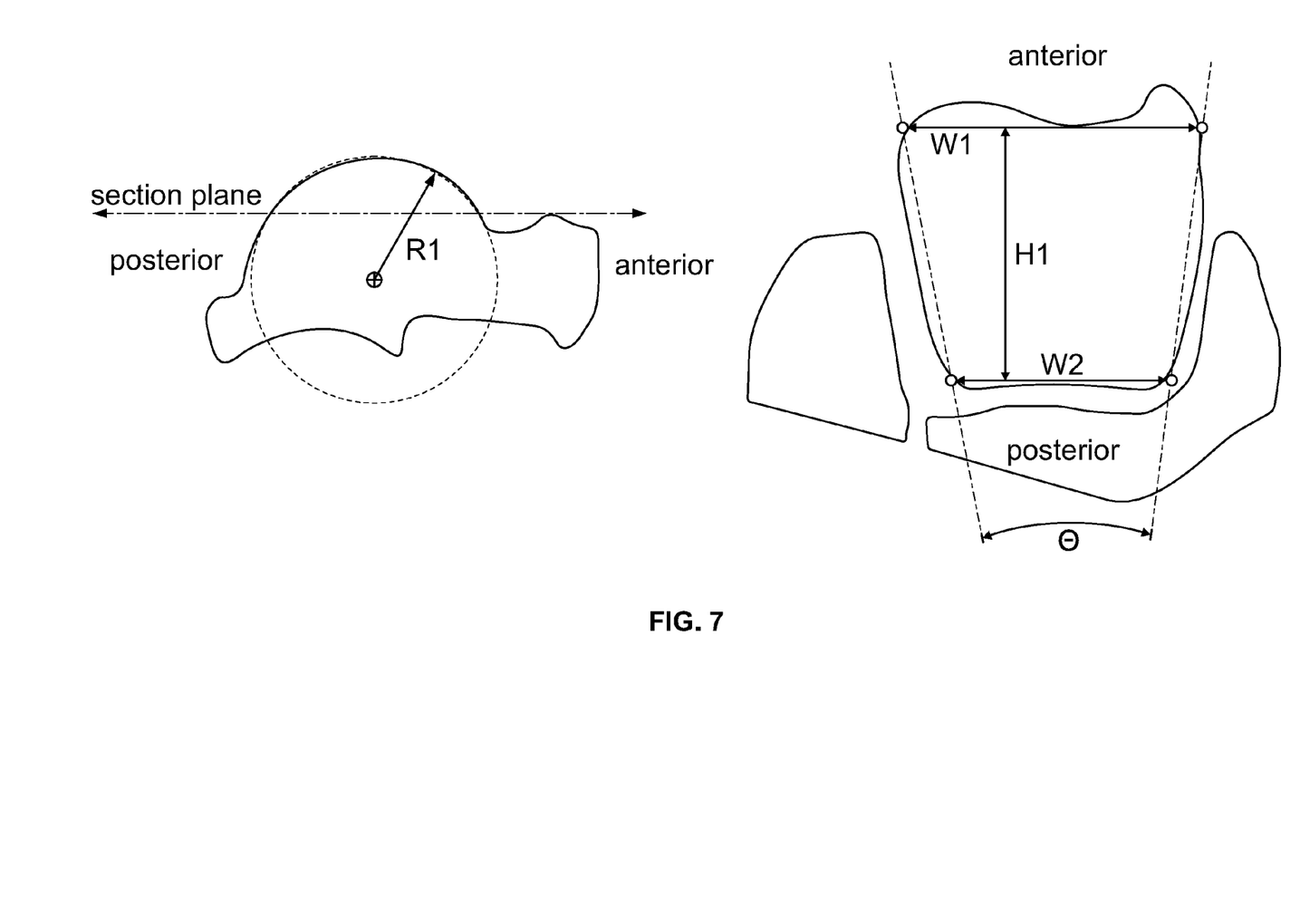
FIG. 7 shows a section plane of a talar bone, showing the first and second widths of talar implants according to some embodiments of the present invention.

In some embodiments, the first width is equal to the width of the posterior portion of the posterior surface of the talus. In some embodiments, the second width is equal to the width of the anterior portion of the posterior surface of the talus. Referring to FIG. 7, the first and second widths are calculated using the dimensions of the talus at the section plane shown.

Figure 8A:
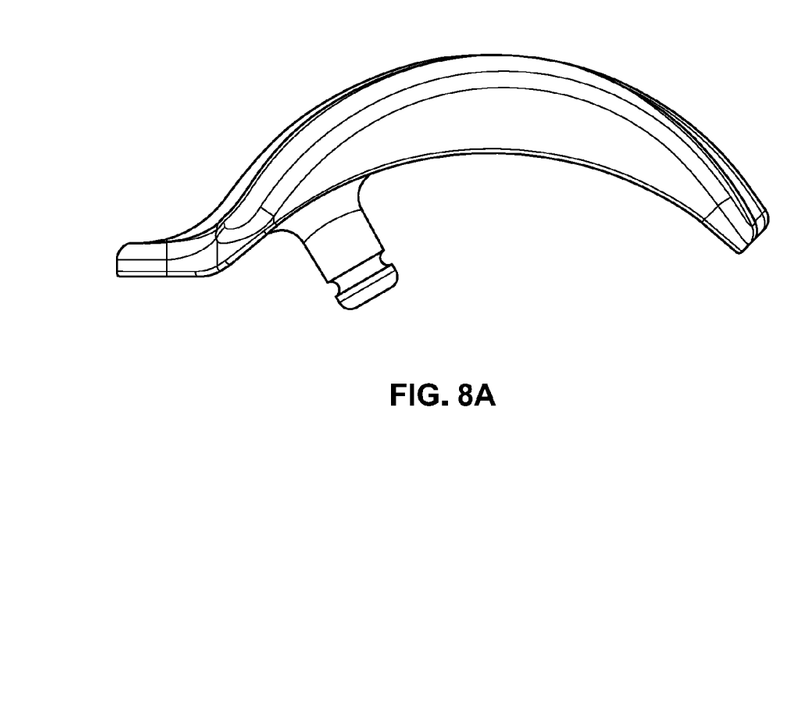
Figure 8B:
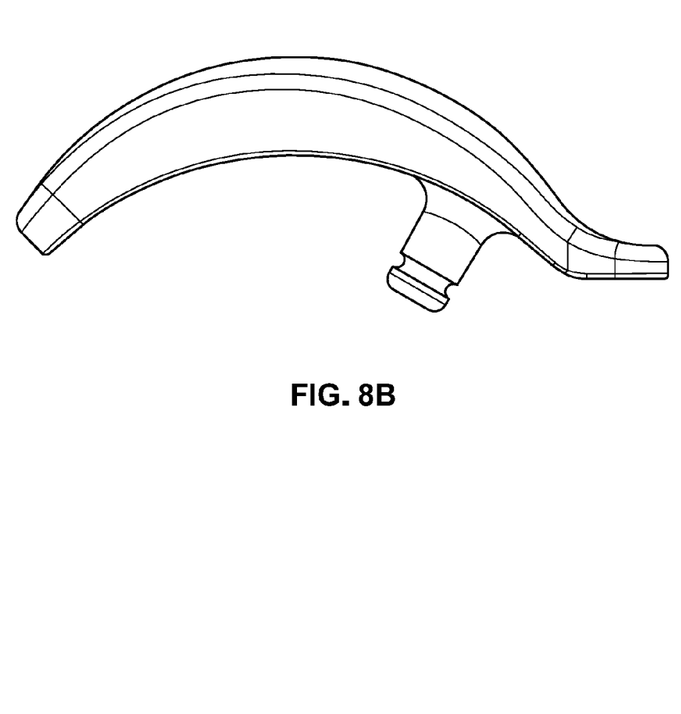

Referring to FIG. 8, in some embodiments, the talar implant is sufficiently designed to restore tension to the tibio-talar joint in the neutral position through the use of arcs that are aligned along the mid-plane of the talar implant in the sagittal plane with different radii. In an embodiment, the arc that defines the articular surface has a smaller radius than the arc defining the inferior surface.

Figure 9:
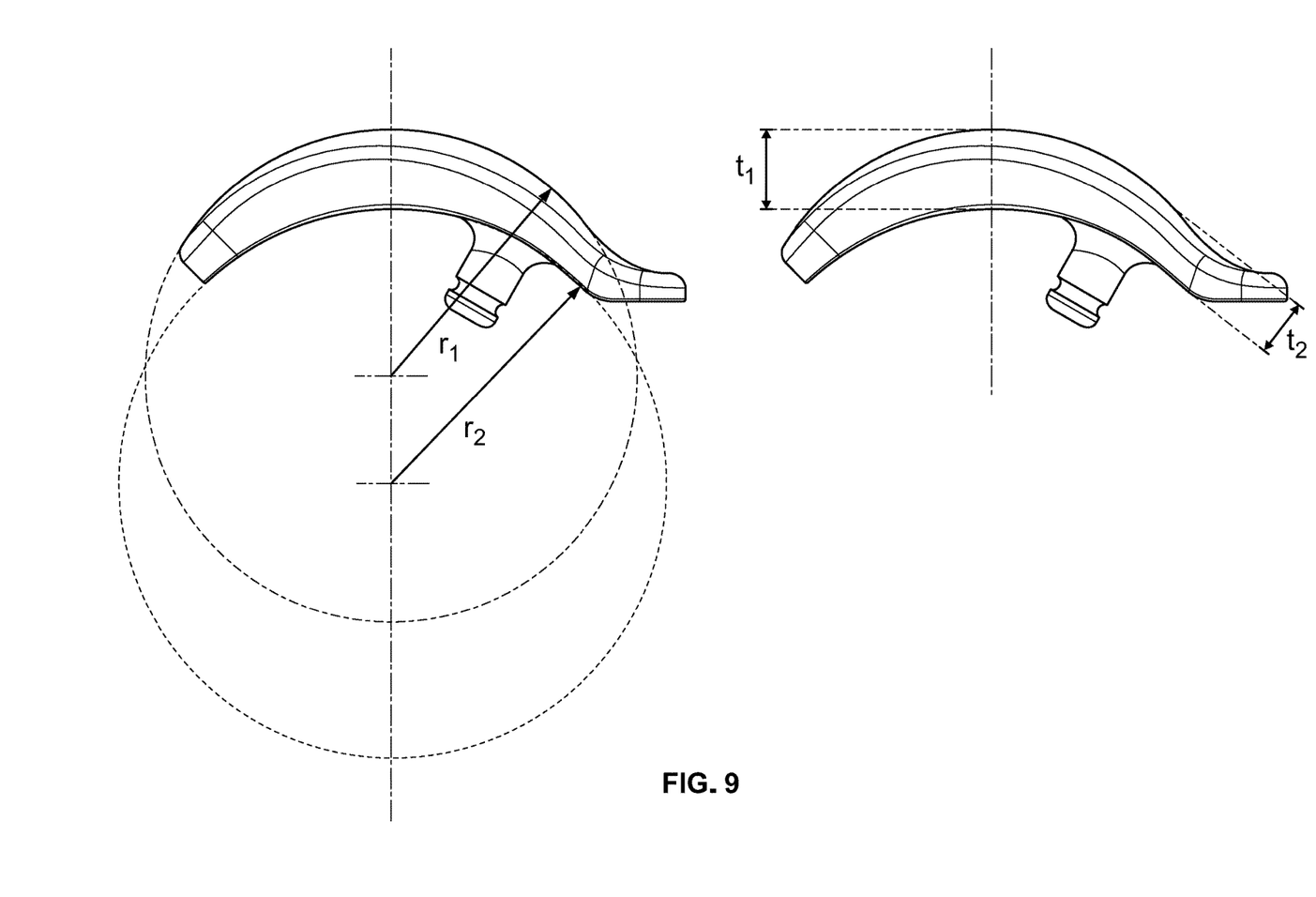
FIG. 9 shows medial views of a talar implant according to some embodiments of the present invention. $r_1$ denotes the at least one first radius. $r_2$ denotes the at least one second radius. $t_1$ denotes the thickness of the talar implant at the plane where the center of the arc having the at least one radius and the sencer of the arc having the at least one second radius align. $T_2$ denotes the thickness of the talar implant at the anterior portion.

Referring to FIG. 9, in some embodiments, the articulating surface of a talar implant of the present disclosure is defined by an arc with a first radius ($r_1$) and the bone interface surface of the talar implant is defined by an arc with at least one second radius ($r_2$). The first radius ($r_1$) is smaller than the at least one second radius ($r_2$). In the embodiment shown, the centers of both arcs are aligned at the neutral plane of the talar implant (dashed line in FIGS. 9A and 9B). The center of rotation of the articular surface is located proximal of the center of rotation of the undersurface. As illustrated in the embodiment shown in FIG. 9B, the resulting geometry is thickest in the neutral plane ($t_1$) and becomes thinner toward the extremes of the range of motion ($t_2$). Without intending to be limited to any particular theory, this configuration provides the highest joint tension at the center of the range of motion but a reduced tension at the extremes potentially reducing the risk of overconstraining the joint.

According to some embodiments, the at least one first radius defines a superior surface of the implant that restores the articular surface of the talar dome.

According to some embodiments, the at least one second radius defines an inferior surface of the implant that attaches to the superior surface of the talus, and requiring no removal of talar bone stock.

In some embodiments, the ratio of the at least one first radius to the at least one second radius is less than 1.

In some embodiments, the ratio of the at least one first radius to the at least one second radius is 0.5. In some embodiments, the ratio of the at least one first radius to the at least one second radius is 0.6. In some embodiments, the ratio of the at least one first radius to the at least one second radius is 0.7. In some embodiments, the ratio of the at least one first radius to the at least one second radius is 0.8. In some embodiments, the ratio of the at least one first radius to the at least one second radius is 0.81. In some embodiments, the ratio of the at least one first radius to the at least one second radius is 0.82. In some embodiments, the ratio of the at least one first radius to the at least one second radius is 0.83. In some embodiments, the ratio of the at least one first radius to the at least one second radius is 0.84. In some embodiments, the ratio of the at least one first radius to the at least one second radius is 0.85. In some embodiments, the ratio of the at least one first radius to the at least one second radius is 0.9. In some embodiments, the ratio of the at least one first radius to the at least one second radius is 0.91. In some embodiments, the ratio of the at least one first radius to the at least one second radius is 0.92. In some embodiments, the ratio of the at least one first radius to the at least one second radius is 0.93. In some embodiments, the ratio of the at least one first radius to the at least one second radius is 0.94. In some embodiments, the ratio of the at least one first radius to the at least one second radius is 0.95. In some embodiments, the ratio of the at least one first radius to the at least one second radius is 0.96. In some embodiments, the ratio of the at least one first radius to the at least one second radius is 0.97.

In some embodiments, the at least one first radius is from 15.0 mm to 20.0 mm.

In some embodiments, the at least one first radius is from 17.0 mm to 18.0 mm.

In some embodiments, the at least one first radius is 15.0 mm. In some embodiments, the at least one first radius is 16.0 mm. In some embodiments, the the at least one first radius is 17.0 mm. In some embodiments, the at least one first radius is 18.0 mm. In some embodiments, the at least one first radius is 19.0 mm. In some embodiments, the at least one first radius is 20.0 mm.

In some embodiments, the at least one second radius is from 22.0 mm to 30.0 mm.

In some embodiments, the at least one second radius is from 23.0 mm to 27.0 mm.

In some embodiments, the at least one first radius is 15.0 mm. In some embodiments, the at least one second radius is 22.0 mm. In some embodiments, the at least one first radius is 15.0 mm. In some embodiments, the at least one second radius is 23.0 mm. In some embodiments, the at least one first radius is 15.0 mm. In some embodiments, the at least one second radius is 24.0 mm. In some embodiments, the at least one first radius is 15.0 mm. In some embodiments, the at least one second radius is 25.0 mm. In some embodiments, the at least one first radius is 15.0 mm. In some embodiments, the at least one second radius is 26.0 mm. In some embodiments, the at least one first radius is 15.0 mm. In some embodiments, the at least one second radius is 27.0 mm. In some embodiments, the at least one first radius is 15.0 mm. In some embodiments, the at least one second radius is 28.0 mm. In some embodiments, the at least one first radius is 15.0 mm. In some embodiments, the at least one second radius is 29.0 mm. In some embodiments, the at least one first radius is 15.0 mm. In some embodiments, the at least one second radius is 30.0 mm.

In some embodiments controlling tension across the tibiotalar joint by varying thickness may be created using multiple radii of curvature in the sagittal view to achieve a design whose thickness varies from the center of the range of motion to the limits of the range of motion in a desired way. In some embodiments, a spherical radius or radii may be used to create the desired effect around a center point rather than center axis.

In some embodiments, the center of the arc having at least one first radius is offset from the center of the arc having at least one second radius in at least one plane of the talar implant selected from the group consisting of: a superior/inferior plane, an anterior/posterior plane, and a medial/lateral plane.

In some embodiments, the center of the arc having at least one first radius is offset from the center of the arc having at least one second radius in the superior/inferior plane.

In some embodiments, the center of the arc having at least one first radius is offset from the center of the arc having at least one second radius in the anterior/posterior plane.

In some embodiments, the center of the arc having at least one first radius is offset from the center of the arc having at least one second radius in the medial/lateral plane.

In some embodiments, the offset of the center of the arc having at least one first radius from the center of the arc having at least one second radius is different on the superior surface of the implant than the offset on the inferior surface of the implant.

In some embodiments, the offset of the center of the arc having at least one first radius from the center of the arc having at least one second radius is different on the medial side of the implant than the offset on the lateral side of the implant.

In some embodiments, the offset of the center of the arc having at least one first radius from the center of the arc having at least one second radius is different on the superior portion of the implant than the offset on the anterior portion of the implant.

Figure 10:
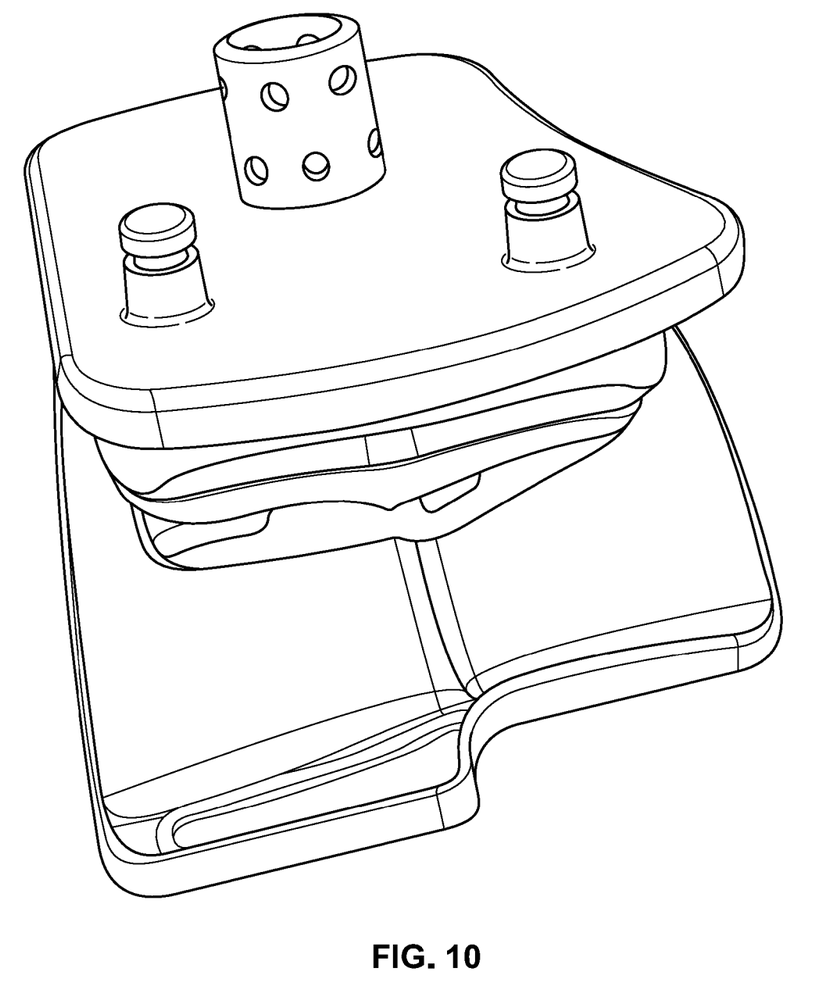
FIG. 10 shows a talar implant and a tibial base component according to some embodiments of the present invention.

Referring to FIG. 10, in some embodiments, the superior surface of the implant is bicondylar. In some embodiments, the mismatch between surfaces accommodates internal/external, inversion/eversion, medial/lateral, and anterior/posterior motion. The two bearing surfaces have different cross-sections (meaning one has a single radius while the other has multiple radii).

In some embodiments, the at least one first radius varies from the medial side of the implant to the lateral side of the implant. In some embodiments, the ratio of the medial first radius to the lateral first radius is 1.10.

In some embodiments, the at least one second radius varies from the medial side of the implant to the lateral side of the implant.

In some embodiments, the tibila base component is configured to attach to the distal tibia after a transverse cut is made and three peg holes are prepared. In some embodiments, the tibial base is symmetrical, allowing it to be used for both right and left ankles.

In some embodiments, the talar implant is manufactured from a cobalt-chromium alloy having a trabecular metal distal surface. Alternatively, in some embodiments, the talar implant includes a thin interlayer of titanium.

In some embodiments, the inferior surface further comprises at least one peg configured to anchor the talar implant to the superior surface of the talus.

In some embodiments, the tibial base component is made from a titanium alloy diffusion bonded to a trabecular metal surface. In some embodiments, the proximal surface of the tibila base component includes three pegs to facilitate stability. Although not visible, an articular surface, manufactured from a polyethylene material, may be mounted to the undersurface of the tibial base component. The polyethylene articular surface can be available in different thicknesses to facilitate proper ligament balancing. The polyethylene articular surface articulates with a talar component (implant) of the present disclosure (bottom component).

In some embodiments, an implant configured according to the present invention may be utilized in other joints aside from the ankle including, but not limited to, shoulder, knee, hip, spine, fingers or toes.

Figure 11:
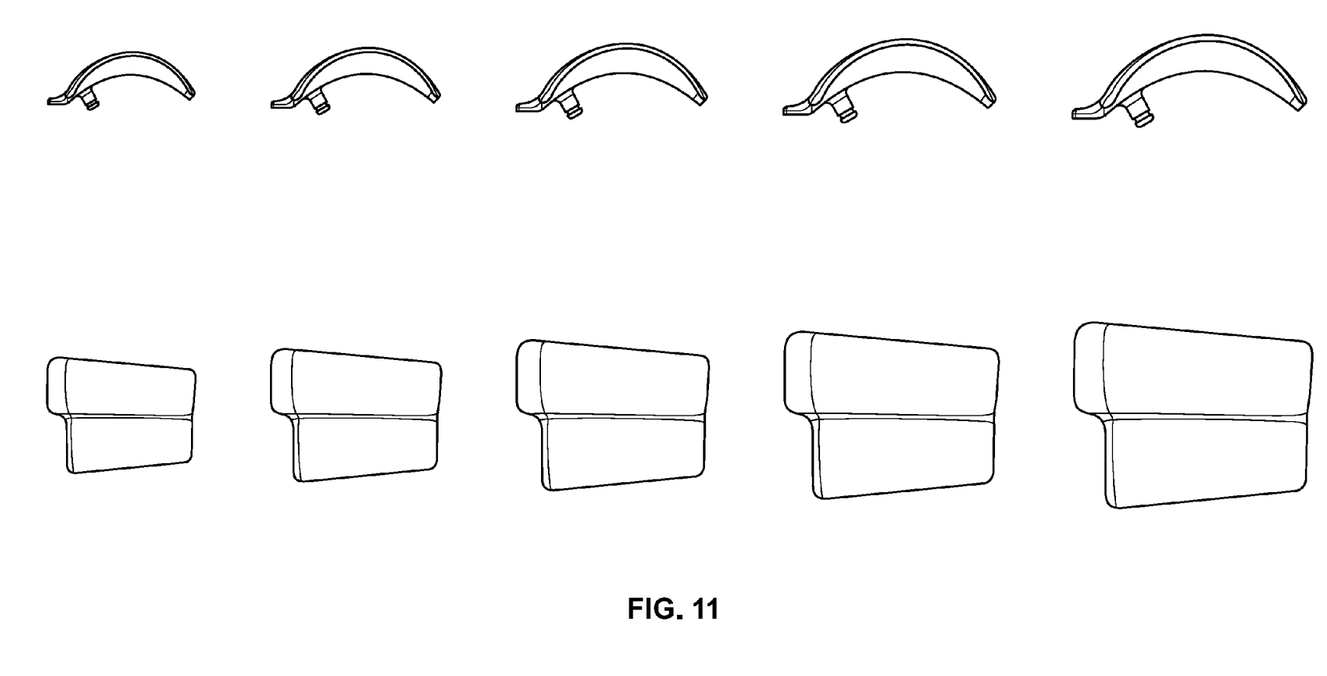
FIG. 11 shows medial views (top row), and a plan view (bottom row) of a plurality of talar implants in a kit according to some embodiments of the present invention.

Referring to FIG. 11, in some embodiments, the present invention provides a kit, comprising a plurality of talar implants, wherein an individual talar implant of claim 1 within the plurality differs in at least one property selected from the group consisting of: the at least one first radius, the at least one second radius, the first width, the second width, the offset of the center of the arc having at least one first radius from the center of the arc having at least one second radius in the superior/inferior plane, the offset of the center of the arc having at least one first radius from the center of the arc having at least one second radius in the anterior/posterior plane, and the offset of the center of the arc having at least one first radius from the center of the arc having at least one second radius in the medial/lateral plane, from any of the other individual talar implants of claim 1 within the plurality.

In some embodiments, the kit further comprises a tibial base component.

According to some embodiments, an individual talar implant is selected having the at least one first radius defines a superior surface of the implant that restores the articular surface of the talar dome.

According to some embodiments, an individual talar implant is selected the at least one second radius defines an inferior surface of the implant that attaches to the superior surface of the talus, and requiring no removal of talar bone stock.

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

What is claimed is:

1. A talar implant, comprising:
   a. a superior surface, defined by an arc having at least one first radius;
   b. an inferior surface, defined by an arc having at least one second radius,
   c. a lateral side;
   d. a medial side;
   e. a posterior portion having a first width; and
   f. an anterior portion having a second width;
      wherein the implant is configured to restore a joint tension between a tibio-talar joint in a neutral position,
      wherein the superior surface is separated from the inferior surface by a thickness, defining a height of the medial and lateral sides,
      wherein the at least one first radius is smaller than the at least one second radius,
      wherein a ratio of the at least one first radius to the at least one second radius is in a range of from about 0.60 to about 0.95,
      wherein the center of the arc having at least one first radius is offset from the center of the arc having at least one second radius in at least one plane of the talar implant selected from the group consisting of: a superior/inferior plane, an anterior/posterior plane, and a medial/lateral plane,
      wherein the inferior surface is configured to attach to a superior surface of the talus,
      wherein the anterior portion further comprises an extension configured to provide support, and
      wherein the superior surface of the implant is bicondylar.

2. The talar implant of claim 1, wherein the at least one first radius varies from the medial side of the implant to the lateral side of the implant.

3. The talar implant of claim 1, wherein the at least one second radius varies from the medial side of the implant to the lateral side of the implant.

4. The talar implant of claim 1, wherein the inferior surface further comprises at least one peg configured to anchor the talar implant to the superior surface of the talus.

5. The talar implant of claim 1, wherein the center of the arc having at least one first radius is offset from the center of the arc having at least one second radius in the superior/inferior plane.

6. The talar implant of claim 1, wherein the center of the arc having at least one first radius is offset from the center of the arc having at least one second radius in the anterior/posterior plane.

7. The talar implant of claim 1, wherein the center of the arc having at least one first radius is offset from the center of the arc having at least one second radius in the medial/lateral plane.

8. The talar implant of claim 1, wherein the offset of the center of the arc having at least one first radius from the center of the arc having at least one second radius is different on the superior surface of the implant than the offset on the inferior surface of the implant.

9. The talar implant of claim 1, wherein the offset of the center of the arc having at least one first radius from the center of the arc having at least one second radius is different on the medial side of the implant than the offset on the lateral side of the implant.

10. The talar implant of claim 1, wherein, the offset of the center of the arc having at least one first radius from the center of the arc having at least one second radius is different on the superior portion of the implant than the offset on the anterior portion of the implant.

11. The talar implant of claim 1, wherein the ratio of the at least one first radius to the at least one second radius is less than 1.

12. The talar implant of claim 1, wherein the at least one first radius is from 15.0 mm to 20.0 mm.

13. The talar implant of claim 1, wherein the second radius is from 22.0 mm to 30.0 mm.

14. A kit, comprising a plurality of the talar implants of claim 1,
    wherein an individual talar implant of claim 1 within the plurality differs in at least one property selected from the group consisting of: the at least one first radius, the at least one second radius, the ratio of the at least one first radius to the at least one second radius, the first width, the second width, the offset of the center of the arc having at least one first radius from the center of the arc having at least one second radius in the superior/inferior plane, the offset of the center of the arc having at least one first radius from the center of the arc having at least one second radius in the anterior/posterior plane, and the offset of the center of the arc having at least one first radius from the center of the arc having at least one second radius in the medial/lateral plane, from any of the other individual talar implants of claim 1 within the plurality.

15. The kit of claim 14, further comprising a tibial base component.

16. The kit of claim 14, wherein each of the individual talar implants of claim 1 within the plurality includes a ratio of its at least one first radius to its at least one second radius in a range of from about 0.70 to about 0.95.

17. The talar implant of claim 1, wherein the ratio of the at least one first radius to the at least one second radius is in a range of from about 0.70 to about 0.95.

* * * * *